US009695073B2

(12) United States Patent
DiMascio et al.

(10) Patent No.: US 9,695,073 B2
(45) Date of Patent: Jul. 4, 2017

(54) DUAL BIOCIDE GENERATOR

(71) Applicant: Ecolab USA Inc., St. Paul, MN (US)

(72) Inventors: Felice DiMascio, Rocky Hill, CT (US); Donald O'Brien, Naperville, IL (US)

(73) Assignee: Ecolab USA Inc., St. Paul, MN (US)

( * ) Notice: Subject to any disclaimer, the term of this patent is extended or adjusted under 35 U.S.C. 154(b) by 267 days.

(21) Appl. No.: 14/446,923

(22) Filed: Jul. 30, 2014

(65) Prior Publication Data

US 2016/0029639 A1    Feb. 4, 2016

(51) Int. Cl.
C25B 1/26 (2006.01)
C01B 11/02 (2006.01)
C02F 1/76 (2006.01)
A01N 59/00 (2006.01)
A61L 2/18 (2006.01)
C25B 1/16 (2006.01)
C25B 9/10 (2006.01)
C02F 1/467 (2006.01)

(52) U.S. Cl.
CPC ............... C02F 1/76 (2013.01); A01N 59/00 (2013.01); A61L 2/18 (2013.01); C01B 11/024 (2013.01); C02F 1/4672 (2013.01); C02F 1/4674 (2013.01); C25B 1/16 (2013.01); C25B 1/26 (2013.01); C25B 9/10 (2013.01); C02F 2201/46145 (2013.01); C02F 2303/02 (2013.01); C02F 2303/04 (2013.01); Y02W 10/37 (2015.05)

(58) Field of Classification Search
CPC ................ C25B 1/26; C01B 11/024
See application file for complete search history.

(56) References Cited

U.S. PATENT DOCUMENTS

| 6,059,942 | A  | 5/2000  | Barnes et al. |
| 6,663,902 | B1 | 12/2003 | Hei et al.    |
| 7,087,190 | B2 | 8/2006  | Hei et al.    |
| 7,604,720 | B2 | 10/2009 | Kaczur et al. |
| 7,976,725 | B2 | 7/2011  | Martin        |

(Continued)

FOREIGN PATENT DOCUMENTS

CN       103796958        5/2014
DE    WO 2008125075 A1 * 10/2008  ........... C01B 11/024

(Continued)

OTHER PUBLICATIONS

PCT, "International Search Report and the Written Opinion of the International Searching Authority", issued in connection with International Applicaiton No. PCT/US2015/042721, issued on Oct. 16, 2015.

Primary Examiner — Nicholas A Smith
(74) Attorney, Agent, or Firm — McKee, Voorhees & Sease, PLC

(57) ABSTRACT

Methods and apparatus for generation of dual biocides are provided. The electrolytic generation of chlorine as a biocide is employed for further generation of additional biocides within a single system or generator, including bromine, iodine, chlorine dioxide, fluorine, or chloramines from their respective salts and/or precursors. A single on-site generating system produces a combination of biocides for applications of use providing cost, safety and efficacy improvements. Methods of using the disinfecting biocides provide a synergistic effect through simultaneous or sequential applications.

19 Claims, 6 Drawing Sheets

(56) References Cited

U.S. PATENT DOCUMENTS

| | | |
|---|---|---|
| 8,262,872 B2 | 9/2012 | Joshi et al. |
| 8,268,159 B2 | 9/2012 | Balagopal et al. |
| 8,394,253 B2 | 3/2013 | Peters et al. |
| 2002/0008040 A1 | 1/2002 | Yamamoto |
| 2005/0079121 A1* | 4/2005 | DiMascio .............. C25B 1/22 423/477 |
| 2008/0181815 A1 | 7/2008 | Cheng et al. |
| 2010/0056628 A1 | 3/2010 | Stockel et al. |
| 2012/0121731 A1 | 5/2012 | Peters et al. |
| 2012/0305494 A1 | 12/2012 | DiMascio |
| 2014/0054239 A1 | 2/2014 | Vineyard et al. |
| 2014/0086822 A1 | 3/2014 | Martens et al. |

FOREIGN PATENT DOCUMENTS

| | | |
|---|---|---|
| WO | 2007064850 | 6/2007 |
| WO | 2010063433 | 6/2010 |
| WO | 2011105985 | 9/2011 |
| WO | 2013019427 A1 | 2/2013 |
| WO | 2013065797 | 5/2013 |
| WO | 2013089366 | 6/2013 |
| WO | 2013093915 A1 | 6/2013 |

* cited by examiner

DUAL BIOCIDE GENERATOR

FIELD OF THE INVENTION

The invention relates to methods and apparatus for generation of biocides. The invention relates to the generation of electrolytic chlorine as a biocide for use in cleaning and disinfecting as well as use as an oxidizing agent to generate additional biocides. In particular, electrolytic chlorine is used to generate sources of bromine, iodine, chlorine dioxide, flourine, or chloramines from their respective salts and/or precursors. Methods of use of dual biocides (also referred to as disinfectants) are employed to produce a synergistic effect through simultaneous or sequential applications providing enhanced pathogen inactivation in comparison to use of a single biocide.

BACKGROUND OF THE INVENTION

Chlorine is commonly used as a disinfectant and available as a gas, liquid or solid form dissolved in water. Common examples include sodium hypochlorite (liquid), calcium hypochlorite (solid), and lithium hypochlorite (solid). Additionally, chlorinated isocyanurates are a family of chemical compounds that, when in contact with water, release hypochlorous acid. Common examples include dichloroisocyanurate and trichloroisocyanurate. The amount of available chlorine differs between the forms, as shown:

| Chemical | Available Chlorine (as HOCl) |
| --- | --- |
| Chlorine Gas | 100% |
| Sodium Hypochlorite Liquid | 5 to 15% |
| Lithium Hypochlorite Solid | 35% |
| Calcium Hypochlorite Solid | 65 to 70% |
| Sodium Dichloroisocyanurate Solid | 56 to 62% |
| Trichloroisocyanurate Solid | 90% |

Such chlorine disinfectants are commonly used to eliminate waterborne pathogens, including for example, enteric, pathogenic, and biofilm forming organisms. Waterborne pathogens can include: filamentous, corrosive, non-spore forming and/or spore forming bacteria; pathogenic bacteria, pathogenic viruses, parasitic protozoa, mycotoxins, algae, spore forming fungi/molds, yeasts and/or mollusks. However, there are known limitations associated with using chlorine sources as a disinfectant, including both stability and safety concerns. For example, chlorine gas is delivered in pressurized bulk containers. These containers range in size from rail tank cars and road tank trucks down to 150-lb cylinders. They are dangerous to handle and store and require compliance with strict handling and storage requirements and therefore are being phased out by certain government regulations (e.g. U.S. Department of Homeland Security Chemical Facility Anti-Terrorism Standards (CFATS)).

Liquid sodium hypochlorite (bleach) solutions present storage limitations as they tend to naturally decompose depending on the storage temperature, its age, concentration, and contaminants it may contain. The decomposition is accelerated upon exposure to sunlight, in addition to often containing caustic stabilizing agents.

There are also limitations associated with using solid chlorine compositions, such as pucks, tablets, pellets, and granular compositions. In particular, the solid compositions contain a lower amount of available chlorine and therefore a higher percentage of inert ingredients (e.g. stabilizers, binders, and salts). As a result, the delivered chlorine has an effect on water chemistry, including for example, alkalinity, water hardness, pH, total dissolved solids (TDS), total settable solids (TSS) and/or conductivity. In many instances, the effects or changes in water chemistry are not desirable as they can affect product quality, reaction efficiency, and/or process controls. For example: chlorine gas will decrease process water pH due to the hydrochloric acid produced when the chlorine gas is dissolved in the water; hydrochloric acid (HCl) will lower water pH; salt (NaCl) byproduct will increase conductivity or TDS in the process water; use of calcium hypochlorite, lithium hypochlorite, or chlorinated isocyanurates adds significant hardness and/or stabilizing and binding agents into water. Still further, chlorine used as a biocide results in generation of disinfection byproducts (DBP) due to the non-selective oxidation and substitution of chlorine species.

A further limitation of use of chlorine biocides involves the control reliability of processes using bleach solutions (e.g. 12.5%) due to natural bleach degradation pathways, wherein bleach forms sodium chloride (NaCl) and sodium chlorate (NaClO3) and the reaction rate increases with increasing temperature. Control reliability is also impacted by a second bleach degradation pathway, where trace metals (e.g. iron, nickel, copper, and cobalt form insoluble metal oxides) and light cause bleach to catalytically decompose to oxygen ($O_2$) and sodium chloride (NaCl). This degradation results in a decrease in available free chlorine, off-gassing and by-product formation (e.g. chloride (Cl—) and chlorate (ClO3-) ions).

The use of chlorine bleach as an oxidant to form other biocides, such as chlorine dioxide, bromine, chloramine, iodine, and fluorine is known. However, the stability limitations associated with chlorine make it difficult to effectively and efficiency produce other biocides. For example, any chlorine forms used as oxidizing agents result in the natural degradation decreasing product concentration, production of a product with excess chloride ions leading to corrosion, producing acidic and/or unstable products, and/or resulting in a process that is unstable or dangerous to operate. Still further, chlorine sources with impurities (e.g. salts, stabilizers, binders) will result in biocide products with impurities. Accordingly, biocides produced from conventional reactions with chlorine are unpredictable without stable and pure chlorine. Therefore, there remains a need for methods of on-site generation of chlorine to resolve these stability issues and provide a chlorine source to overcome these limitations.

An object of the present invention provides methods for generating a stable source of chlorine to effectively and efficiently produce additional biocides.

A further object of the invention is to provide dual biocides at a point of use or onsite generation to overcome the stability and safety concerns with transporting biocides.

A still further object of the invention is to overcome stability and safety concerns associated with solid biocide chemistry, including reduced chemical handling concerns and elimination of risks associated with runaway chemical reactions involving solid biocides which are improperly fed and/or fed with incorrect feed equipment.

Still further, there remains a need for enhanced disinfecting formulations providing more effective disinfection due to resistance of pathogens. Therefore, an object of the present invention is to provide dual biocides (one or more) for enhanced disinfectant efficacy.

Other objects, advantages and features of the present invention will become apparent from the following specification taken in conjunction with the accompanying drawings.

BRIEF SUMMARY OF THE INVENTION

An advantage of the invention is the onsite production of dual biocide disinfectants for the sequential and/or simultaneous application to achieve synergistic efficacy. The methods and apparatus provide user select ability for electrolytic generation of chlorine and additional biocides, including bromine, iodine, fluorine, chlorine dioxide, or chloramines from their respective salts and/or precursors. It is an advantage of the present invention that a synergistic disinfectant formulation is supplied without the need to include other disinfectants, such as quaternary ammonium compounds, providing benefits and advantages over single conventional disinfectants.

In an embodiment, the present invention provides methods of generating a dual biocide comprising: providing a divided electrolytic cell; supplying a sodium chloride solution to the cell to generate an elemental chlorine and a sodium hydroxide stream in the electrolytic cell; combining at least a portion of the elemental chlorine stream with the sodium hydroxide stream to form a sodium hypochlorite solution; and combining at least a portion of the elemental chlorine stream with a salt solution.

In an additional embodiment, the present invention provides methods of providing a dual biocide at a point of use comprising: providing an electrolytic cell having an anode chamber and a cathode chamber separated by a cation exchange membrane, wherein the cathode chamber contains a negative electrode, or cathode, and the anode chamber contains a positive electrode, or anode, supplying a sodium chloride solution to the cell to generate an elemental chlorine and a sodium hydroxide stream in the electrolytic cell; applying a potential to the electrolytic cell; combining at least a portion of the elemental chlorine stream with the sodium hydroxide stream to form a first biocide sodium hypochlorite solution; combining at least a portion of the elemental chlorine stream with a salt solution, wherein the salt solution contains a member selected from the group consisting of chlorite, bromide, iodide, fluoride, ammonia and combinations thereof; generating a second biocide selected from the group consisting of chlorine dioxide, bromine, iodine, fluorine, chloramine and combinations thereof; and providing the biocides to an application of use.

In additional embodiments, the present invention provides methods of chlorinating, disinfecting and/or sanitizing employing a biocide generated at a point of use comprising: generating at least one biocide selected from the group consisting of chlorine, sodium hypochlorite, chlorine dioxide, bromine, iodine, fluorine, chloramines and combinations thereof at a point of use; and contacting a surface and/or water source in need of chlorination, disinfection and/or sanitation with the biocide.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
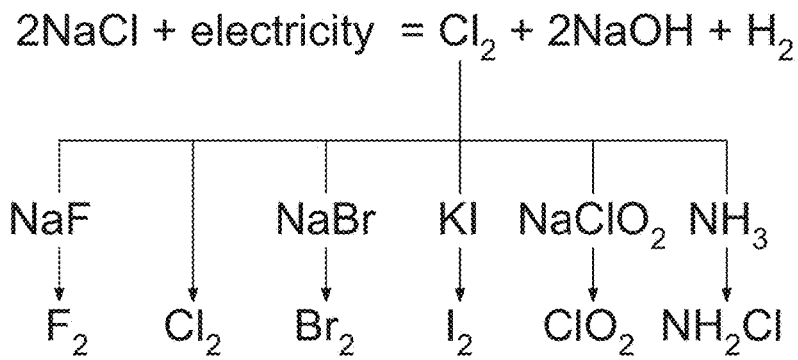
FIG. 1 shows a diagram of the generation of electrolytic chlorine which can be further used as an oxidizing agent to generate bromine, iodine, fluorine, chlorine dioxide, and/or chloramines from their respective salts or precursors.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to dual biocide generation, compositions and methods of use thereof. The synergistic disinfectant compositions and methods of use have many advantages over any single conventional disinfectant, including for example cost benefits, efficacy benefits, and stability and safety benefits due to the onsite generation according to the invention.

The embodiments of this invention are not limited to particular apparatuses for production of the dual biocides, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, apparatuses, and compositions of the present invention may comprise, consist essentially of, or consist of the components and ingredients of the present invention as well as other ingredients described herein. As used herein, "consisting essentially of" means that the methods, apparatuses and compositions may include additional steps, components or ingredients, but only if the additional steps, components or ingredients do not materially alter the basic and novel characteristics of the claimed methods, apparatuses, and compositions.

It should also be noted that, as used in this specification and the appended claims, the term "configured" describes an apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

As referred to herein, biocides are disclosed for use as disinfectants. Public health antimicrobial pesticides are generally placed in one of three categories, depending on the use pattern and the required effectiveness. In decreasing order of effectiveness, these are sterilants, disinfectants and sanitizers. Sterilants completely destroy or eliminate all forms of microbial life in the inanimate environment, including all forms of vegetative bacteria, bacterial spores, fungi, fungal spores, and viruses. They are typically used on critical and semi-critical devices in a medical environment. Disinfectants are substances that destroy or eliminate a specific species of infectious or other public health microorganisms, but not necessarily bacterial spores, in the inanimate environment. Sanitizers are the least potent of the antimicrobial public health pesticides. They reduce the number of microorganisms by orders of magnitude, but may not kill all of them under the test conditions. As set forth according to the methods of the invention, biocides are particularly well suited for use as disinfectants.

Methods of Generating Dual Biocides

According to an embodiment of the invention, chlorine, sodium hypochlorite and/or additional biocides are electrolytically generated at a point of use providing a biocide suitable for use (and generating sodium hypochlorite for use) as well as providing an inexpensive and readily-available oxidizer source for generating additional biocides. As shown in FIG. 1, electrolytic chlorine can be used as an oxidizing agent to generate bromine, iodine, fluorine, chlorine dioxide, and/or chloramines from their respective salts or precursors. As illustrated, using the generated chlorine ($Cl_2$) as an oxidizer, at least five other biocides can be generated by their respective salts or precursors; bromine ($Br_2$) from sodium bromide (NaBr), iodine ($I_2$) from potassium iodide (KI), chlorine dioxide ($ClO_2$) from sodium chlorite ($NaClO_2$), fluorine ($F_2$) from sodium fluoride (NaF) and chloramine ($NH_2Cl$) from ammonia ($NH_3$).

In an aspect, the methods comprise, consist and/or consist essentially of supplying a sodium chloride solution to a divided electrolytic cell, producing two effluent streams (i.e. elemental chlorine and sodium hydroxide) from the electrolytic cell, combining at least a portion of the elemental chlorine stream with the sodium hydroxide stream to form a sodium hypochlorite solution and/or combining at least a portion of the elemental chlorine stream and/or sodium hydroxide stream with a salt (or biocide precursor) solution to generate a dual biocide. In an aspect, the salt solutions contain chlorite, bromide, iodide, fluoride, or ammonia to respectively form a chlorine dioxide, bromine, iodine, fluorine, or chloramine solution. When generating elemental chlorine, a salt solution can be added to the elemental chlorine at the stoichiometric amount or less than the stoichiometric amount. At the stoichiometric amount bromine, chlorine dioxide, iodine, fluorine, or chloramine will exist alone. At less than the stoichiometric amount, chlorine can coexist at any level with any one of the other biocides. For example, adding sodium bromide at 50% of the stoichiometric amount will generate a biocide consisting of 50% chlorine and 50% bromine. Similarly, adding sodium chlorite at 25% of the stoichiometric amount will generate a biocide consisting of 75% chlorine and 25% chlorine dioxide. In further aspect, the methods may further comprise, consist and/or consist essentially of employing control and monitoring systems.

In an aspect, the dual biocide generator systems referred to herein refer to all component, including for example electrolytic cell, reaction tower(s), storage tank(s), conduits or delivery lines for reagent(s) and generated biocides, mixing units, control systems, meters, sensors, valves and/or pumps, and discharge devices (e.g. nozzles for applying, spraying, and dosing the biocides generated according to the invention at a point of use). The dual biocide generator system may be provided in a variety of portable and/or fixed systems.

Electrolytic Cells Employed

The methods include providing at least one electrolytic cell, or also referred to as an electrolytic electrochemical cell or al electrolytic chlorine generator. Preferably a single electrolytic cell is employed. Chlor-alkai cells are particularly suited for application according to the invention; however as one skilled in the art will appreciate any electrolytic cell or generator producing molecular chlorine and sodium hydroxide may be employed as described herein. Numerous variations to the cell known to those skilled in the arts of electrolytic cells are suitable for use in generating the dual biocides. The electrochemical cell is divided by a membrane to separate an anode chamber from a cathode chamber. In an aspect, the electrochemical cell is divided by a cation exchange membrane separating the anolyte and catholyte. As a result, the cell has separate flow channels for the anolyte fluid to come in electrical contact with the anode and the catholyte fluid to come in electrical contact with the cathode. In some aspects, the membrane has one or more of the following properties: thickness from about 10 to about 500 μm; ion exchange capacity from about 0.8 to about 2.1 meq/mL; selectivity of from about 90 to 99%; specific area resistance from about 0.2 to 10 Ohm-$cm^2$; stability at pH from about 1 to about 14. In a preferred aspect, a cation exchange membrane with a cross-linked perfluorinated polymer backbone with sulfonic acid groups attached to it is employed. Beneficially, such cation exchange membranes having the acid functionality provide channels for cations to migrate through the polymer matrix while blocking the passage of anions In an aspect the anode is metal. Preferably, the anode is coated with a catalyst to suppress the decomposition of water and facilitate the formation of elemental chlorine. In an aspect, the anode provides at least a 90% efficient in converting chloride ion to chlorine.

In an aspect the cathode is metal. Preferably, the cathode is a stainless steel (e.g. 316L stainless steel), titanium or nickel-alloy.

In an aspect, the methods of the invention of employing the electrolytic cell operate at a temperature up to about 120° F. to preserve the stability of the chlorine.

The methods according to the invention include providing an anolyte solution. In an aspect, the anolyte is a sodium chloride solution. The sodium chloride solutions may be diluted to concentrations of about 100 g/L or less, of about 50 g/L or less, or about 30 g/L or less.

The methods according to the invention include providing a catholyte. In an aspect, the catholyte is a water source. In an aspect the catholyte is a softened water source, or preferably softened potable water having a conductivity of less than about 1,000 μs/cm.

In an aspect of the methods of the invention, an anolyte solution of sodium hydroxide is separated from the acidic anolyte (e.g. chlorine). In an aspect, the cations pass through the cation exchange membrane from the acidic anolyte to the caustic catholyte without causing detrimental precipitation to the membrane. In an aspect, the flow direction of anolyte and catholyte is parallel to the electrodes. In an aspect, a softened water source may be employed to remove water hardness ions (e.g. calcium, magnesium) from the feed water.

The methods include providing a potential to the electrodes of the electrolytic cell. In an aspect, when a potential is applied to the electrodes electrostatic attraction for cations (e.g. sodium ions) to the cathode and away from the anode occurs, while attraction for the anions (e.g. chloride ions) to the anode and away from the cathode also occurs. According to the electrochemical process described herein and recognized by those skilled in the art, chloride ions contacting the anode are subject to electrochemical reaction if the anode potential is sufficiently high. In an aspect, the operational current density of the electrolytic cell is less than 1.0 amp per square inch.

In an aspect of the invention, the methods beneficially produce a concentration of free available chlorine (FAC) in the electrolytic cell of less than about 12 grams per liter (g/L), more preferably less than about 8 g/L, and most about less than 5 g/L of FAC.

In an aspect, upon generation of the chlorine within the electrolytic cell the effluent stream may be diluted with water. In some aspects the chlorine and/or sodium hydroxide are diluted prior to an application of use in embodiments where dual (or at least two) biocides are dispensed from a system. In other aspects, the dilution takes places by adding water inline prior to dosing the chlorine into the reaction tower for generation of the dual biocide. In some aspects, the chlorine and/or sodium hydroxide is diluted to meet safety and/or regulatory requirements. For example, chlorine may be diluted to an effective use concentration of less than about 1.0% or about 1,000 mg/L.

Generating Oxidizing Biocides

Figure 2:
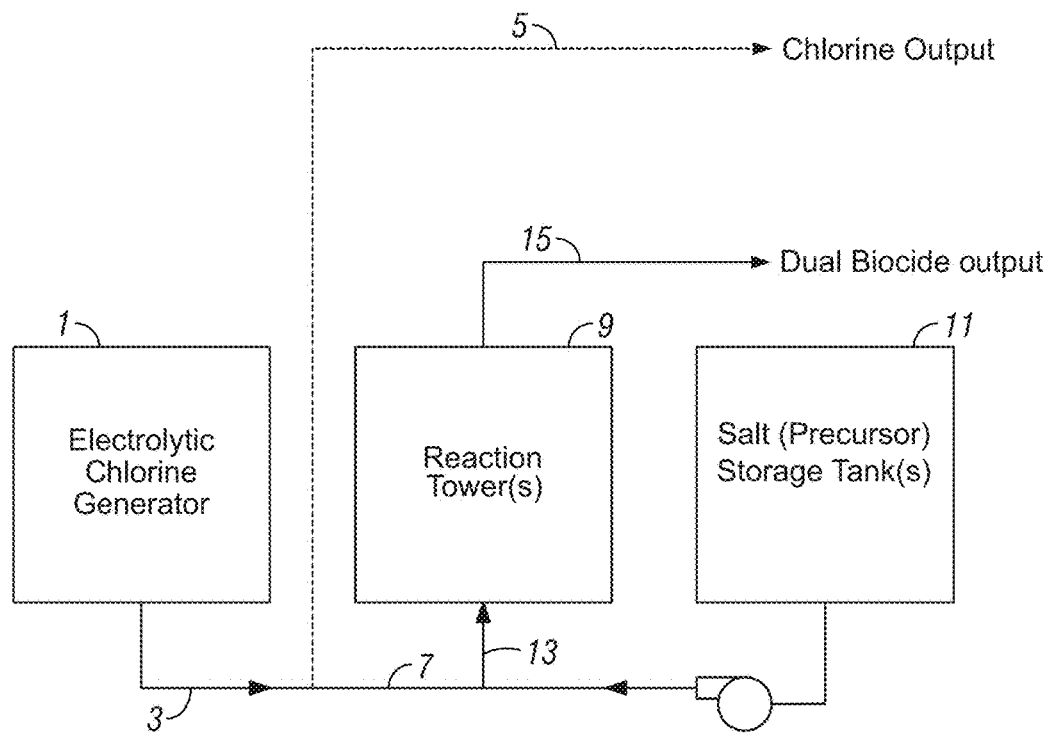
FIG. 2 shows a non-limiting diagram of an embodiment of the invention wherein electrolytic chlorine is generated as an output from an electrolytic cell along with the generation of additional biocides in a reaction tower at a point of use with the electrolytic chlorine generator to generate bromine, iodine, fluorine, chlorine dioxide, and/or chloramines from their respective salts or precursors.

As shown in FIG. 2, in an aspect of the invention, the methods include electrolytically-generating chlorine 3 employing the electrolytic cell or chlorine generator 1. The elemental chlorine stream (and optionally the sodium hydroxide stream for the production of sodium hypochlorite) 7 are combined with a salt (or biocide precursor) solution 13 to generate a dual biocide 15. In an aspect, the salt solutions contain chlorite, bromide, iodide, ammonia or fluoride to respectively form a chlorine dioxide, bromine, iodine, chloramines or fluorine solution.

The salt solution 13 can be stored in a storage tank 11 and added to a reaction tower 9 in fluid connection with the electrolytic chlorine generator 1 which has provided the chlorine 7 for oxidation of the salt solutions in the reaction tower 9 and thereafter at any time providing the dual biocide 15 for applications of use. As further depicted in FIG. 2, there can be an outlet stream from the electrolytic chlorine generator 1 split into two separate streams 5, 7 where one stream provide chlorine (and optionally sodium hydroxide for generation of sodium hypochlorite) for dosing to an application of use 5 and second stream 7 provides chlorine for oxidation of the salt solutions 13 in the reaction tower 9 to generate a dual biocide 15.

Alternatively, the salt solution can be stored in a salt (precursor) storage tank 11 and added directly to a discharge line of the electrolytic cell (i.e. chlorinator or generator) wherein the formation of the additional biocide occurs inline to a point of use delivery for a single biocide (not depicted).

As referred to herein reaction towers may be formulated into a variety of shapes and dimensions suitable for onsite at a variety of locations. As a result, the reaction towers may vary in size and dimension depending on the number of reaction columns contained therein (dependent upon the number of distinct biocides to be generated according to the methods of the invention).

In some aspects, the systems suitable for use according to the invention may include a plurality of reaction towers 9 and salt storage tanks 11, such that a system is configured to product more than one dual biocide (e.g. a combination of chlorine, chlorine dioxide, bromine, iodine and/or chloramine) from a single system.

In an aspect, the storage tank(s) holding salt solutions (or precursor solutions) in fluid connection with the delivery line and/or reaction tower for the generation of the additional biocide can be automated and/or manually adjusted to start/stop the injection of the salt solutions to the chlorine.

In general the oxidizing reaction between the chlorine and the salt (precursor) solution requires from about 30 seconds to about 30 minutes. In some aspects, the reaction within the reaction tower takes from about 1 minute to about 30 minutes. As one skilled in the art will appreciate, the reaction time will differ depending upon the biocide to be generated, quantity to be generated, and the like.

In an aspect, upon generation of the dual biocide water may be added to dilute the biocide. In some aspects the biocides are diluted prior to an application of use. In some aspects, biocide(s) may be diluted to meet safety and/or regulatory requirements. For example, biocide(s) may be diluted to an effective use concentration of less than about 1.0% or about 1,000 mg/L. In a preferred aspect, the dilution takes places by adding water inline, such as prior to dosing the biocide from a system.

In an aspect, the methods may further comprise, consist of and/or consist essentially of an additional step (and in some aspects an initial step) of determining the "oxidant demand" of a system and/or water source in need of biocidal treatment. As referred to herein, "oxidant demand" represents the quantity of biocide that reacts with constituents on the surface and/or water source within a set time. The oxidant demand of a system identifies biocide requirements to disinfect a system, as it provides information on the water quality and microorganism level to determine the effective dosage of biocides to be used in the application. The oxidant demand of a system is then suitable for use for a user or process controller for a system generating the oxidizing biocide.

In an aspect, the methods may further comprise, consist of and/or consist essentially of an additional step of conducting a bacteriological water analysis. Such analysis as referred to herein estimates the numbers of bacteria present and, if needed, identifying the type of bacteria. Exemplary methods include: multiple tube method, ATP testing, plate count, membrane filtration, and pour plates.

Figure 3:
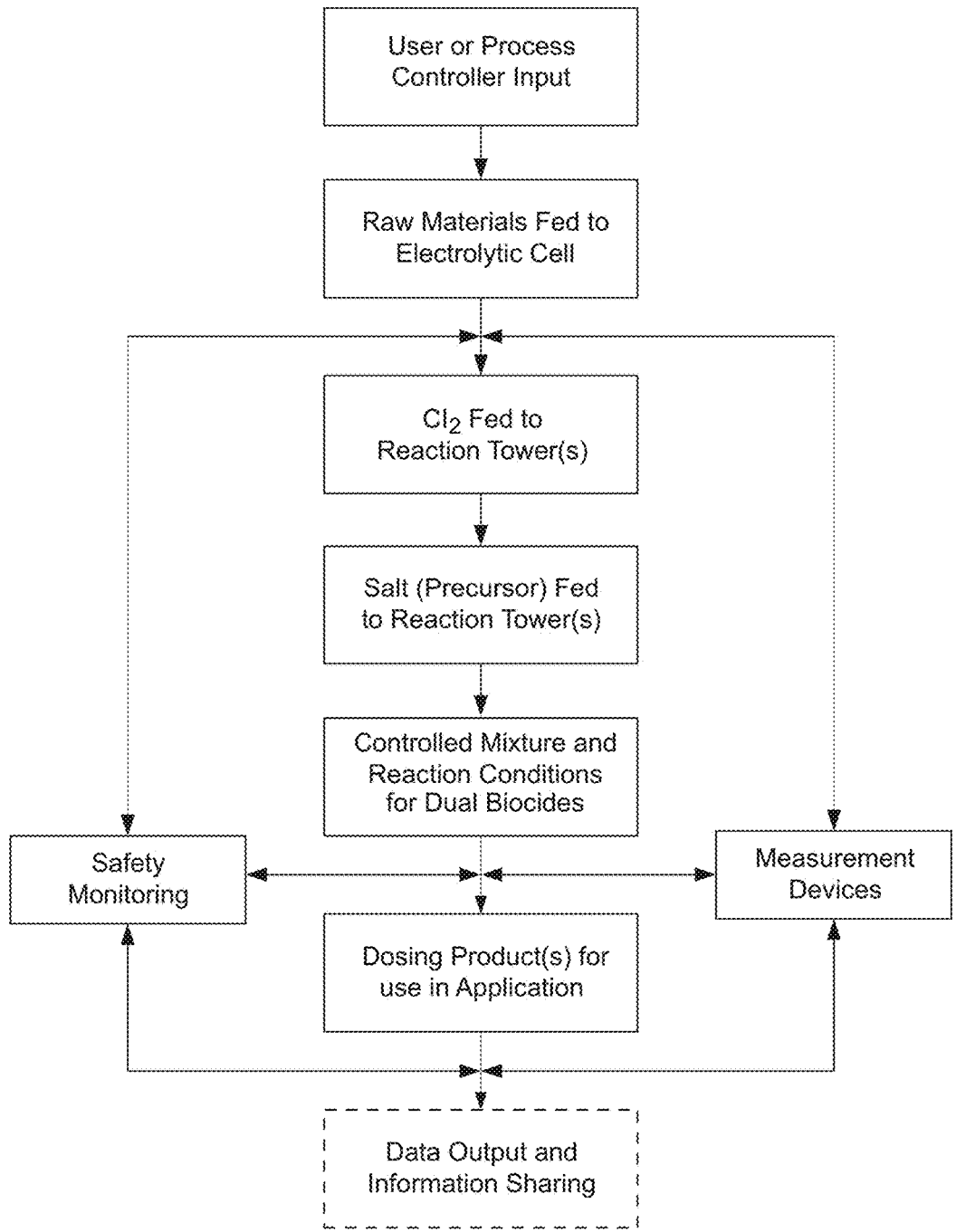
FIG. 3 shows a diagram overview of methods of generating biocides according to embodiments of the invention.

As shown in FIG. 3, in aspects of the invention, the methods of electrolytically-generating chlorine and thereafter employing chlorine for oxidation of additional biocides can be depicted from a process control. A user or process controller inputs a desired dual biocide formulation, volumes, concentration, and the like. Thereafter, raw materials are fed to the electrolytic cell for the generation of chlorine, which is then fed into a reaction tower (which as described above may contain a plurality of reaction vessels suitable for oxidation of various salt solutions to produce a plurality of biocides). Salt (or precursor) solutions are also fed into the reaction tower wherein there are controlled mixture and reaction conditions for the generation of the dual biocides. Reaction conditions which are measured and monitored include for example, temperature, concentration of reactants and generated biocides, and the like. The measuring and monitoring are ongoing processes during the reaction and dosing of the biocides for applications of use. Several methods are available for measuring chlorine, bromine, chlorine dioxide, iodine, fluorine and chloramines residuals. In most situations, it is not necessary to distinguish the type of oxidizing biocide. It is only necessary to know the total residual oxidant (TRO) level since this is what is required for compliance with certain regulatory requirements (e.g. Environmental Protection Agency (EPA), National Pollutant Discharge Elimination System (NPDES)). An exemplary method is the N,N-diethyl-p-phenylenediamine (DPD) method. For example, good microbiological control can be obtained when the TRO is maintained at a trace to 0.1 mg/L free available oxidant (FAO) within the system. Dilution, reactions, etc. will normally result in less than 0.2 mg/L FAO at the final system discharge point. In addition, the methods may further employ various aspects of data output and information sharing.

Control and Monitoring Systems Employed

The methods further include providing a control and monitoring system for the generation of biocides for on-site or on-demand production and use. Beneficially, a control and monitoring system ensures treatment efficacy of the biocides generated and employed according to the methods of the invention. In an aspect, the systems establish a desired biocide(s) concentration (i.e. optimum level for treatment) which provides cost effective treatment, including for example, with respect to energy, water and chemical usage according to the methods of the invention. In another aspect, the systems assess and/or predict treatment behavior on of the systems employed according to the invention. For example, the systems are integrated to obtain information on the conditions of the operational equipment to treat according to the methods. In addition, the systems are integrated to relate this information to operating variables set forth for the system (i.e. pH, temperature, water quality, chemical treatment), providing at least the following benefits: increased operational life of the system, improved efficiency of the system and quality of the system's biocide products, establishes defined maintenance and optimization steps, and reduces operational costs.

As a further benefit, control and monitoring systems provide an integrated safety system for use with the methods of the invention. In an aspect, the control system permits the dosing of biocides in desired quantity, at a desired time, and pursuant to established safety criteria, beneficially resulting in reduced material waste, improved safety, and protection of the environment. For example, the control and monitoring systems allows accurate dosing and generation of biocides such that chemicals and/or contains are not discarded (e.g. due to onsite generation) and there is eliminated need for transportation of hazardous chemicals, etc. As referred to herein, the control and monitoring systems may be performed by manual means, partial automated means, and/or fully-automated means, including manual, digital, and/or analog methods to monitor, process and control the methods of the invention and dual biocide generator systems. These processes can be accomplished in a variety of ways by one skilled in engineering and system design, with substantially automated technologies being a preferred aspect of the invention.

In an aspect, the methods further include employing the control and monitoring systems to provide a user with automated visuals, alarm logs, and historical archives relating to the generation of the chlorine and additional dual biocides according to the invention. A control beneficially provides users real-time information allowing timely corrective actions in the event of any process changes and/or condition changes as it is in communication with the electrolytic cell, reaction tower, storage tanks and delivery lines of the dual biocide generator systems of the invention. As a further benefit, operations are automatically shut down in the event of a user failing to make the corrective actions. Beneficially, such safety systems prevent escalation of biocide generation outside of identified parameters, such as a result of equipment failure, sudden fluctuation in process parameters or human error.

In an aspect, the control and monitoring systems allow use of real-time variable input data regarding conditions such as temperature, level (volume), and flow and pressure (e.g. as measured by transmitters to determine the safe timing for the generation of an oxidizing biocide). In an aspect, control systems are employed for automatically measuring a quantity selected from the group consisting of flow meter output, temperature of the electrolytic cell, brine pump velocity, and incoming water flow rate. In an aspect, the monitoring step is performed using a flow meter, a rotameter, or a pressure transducer, or monitoring a temperature difference across the electrolytic cell via a first thermocouple or thermowell disposed at an inlet of the electrolytic cell a second thermocouple or thermowell disposed at an outlet of the electrolytic cell.

In a further aspect, the controller operates in response to one or more inputs selected from the group consisting of an electrolyte temperature, an oxidant temperature, a current density in the electrolytic cell, a water flow rate, a water pressure, and a brine flow rate. The generator systems according to the invention may therefore further comprise a controller for separately controlling operation of the variable speed brine pump and the water flow control valve.

In a further aspect, the control and monitoring systems ensure chlorine and/or sodium hydroxide (forming sodium hypochlorite) and/or the dual biocides are not delivered at concentrations or use solutions exceeding predetermined concentrations, such as for example 1.0% or about 1,000 mg/L.

Figure 4:
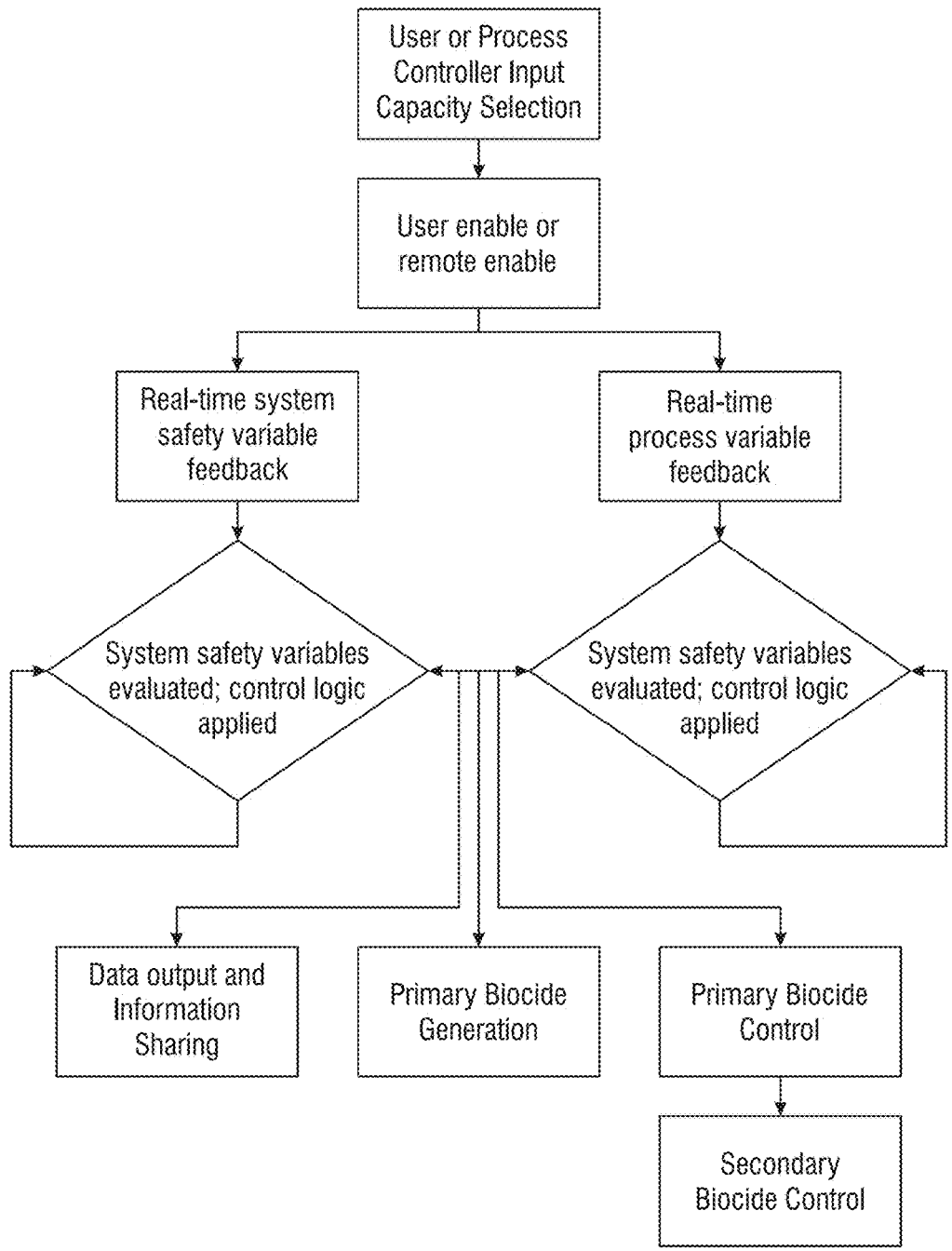
FIG. 4 shows a diagram overview of the control and monitoring systems employed for onsite generation of biocides according to embodiments of the invention.

As shown in FIG. 4, the methods of the invention provide a user or process controlled system for onsite generation of biocides. In an aspect, a user of a process determines the capacity for the dual biocides to be generated. A user or a remote initiation of the process is employed. Both real-time system safety and process variable feedback systems are employed according to the invention. In an aspect, the real-time system safety variable feedback includes the ongoing monitoring of system safety variables (e.g. pH, temperature, water pressure, water flow, salt and/or biocide concentration). The safety variable feedback monitoring evaluates such data points compared to minimum and maximum thresholds that ensure safe operation of the system. Should a condition outside of the safety parameters exist, the on-site generator changes into a safe state, whereby there is an alarming of the user/system of the current condition. The real-time process variable feedback includes the ongoing monitoring of process variables (e.g. pH, temperature, water pressure, water flow, water quality, biocide concentration). The process variable feedback monitoring evaluates such data points in a manner that ensures efficient generation of biocide(s) based on the real-time system conditions. In an aspect, data output from the monitoring may further result in information sharing suitable for a use or process to adjust biocide generation and operations.

Methods of Use

According to an embodiment of the invention, chlorine, sodium hypochlorite, chlorine dioxide, bromine, iodine, fluorine, chloramines, and combinations thereof generated according to the methods of the invention are employed for chlorination, disinfection and/or sanitation. The biocides generated according to the invention are designed to kill all sizes and life stages of organisms, including microorganisms. Accordingly, the dual biocide compositions generated according to the invention find use as sanitizers, disinfectants, preservatives, sterilizers, deodorizers, antiseptics, fungicides, germicides, viracide, tuberculoside and so forth.

The biocides generated according to the invention are effective against a wide variety of microorganisms. These include bacteria in either their vegetative or spore states and including gram negative, gram positive and acid fast bacteria. The compositions of the present invention are also antimicrobially active against bacteria, fungi, spores, yeasts, molds, mildews, protozoans, viruses, and so forth, including lipophilic, non-lipophilic, enveloped and naked RNA/DNA types. Among others, the compositions of the present invention are effective against microbes including, but not limited to, viral members of Parvoviridae, Calciviridae, Herpesviridae, and Paramyxoviridae. Other bacterial organisms against which the compositions of the present invention are active include Enterobacteriaceae, *Mycobacterium* spp leading to tuberculosis (acid fast), Staphylococci including *Staphylococcus aureus* (gram positive), *Streptococcus pneumoniae, Streptococcus agalactiae, Klebsiella pneumoniae, Pseudomonas aeruginosa, Pneumocystic carinii, Listeria monocytogenes, Aspergillus* spp., *Echerischia coli* (gram negative) including O157:H7, *Salmonella* spp, *Bacillus cerius, Chatomium* spp, *Actinomyces pyogenes, Corynebacterium bovis*, human parainfluenza viruses, *Listeria monocytogenes*, nonenveloped double-shelled viruses such as rotaviruses or adenoviruses. *Pseudomonas aeruginosa, Mycoplasma bovis*, respiratory syncytial virus, *Haemophilus influenzae* Type B, other viruses including parvovirus, coxsackie virus or herpes virus, as well as other species of microorganisms and viruses. This list is illustrative of types of microbes which the present invention may be used to treat but is by no means an exclusive list. Both iodine and chlorine dioxide are broad spectrum antimicrobials. One of skill in the art would know what microbes against which such compounds are effective. The present invention envisions other microbes, not listed here, against which such compounds would be active, and does not intend to limit the scope of the invention in any way by such a list.

Beneficially, the application of combinations of biocides overcomes limitations of convention use of single biocides such as chlorine dioxide or sodium hypochlorite, namely use of combinations allows application of otherwise sub-lethal concentrations and/or shorter applications of time while still providing chlorination, disinfection and/or sanitation. As a further benefit of the methods of the present invention, the generation of multiple biocides electrochemically at a point of use eliminates hazards of handling gas cylinders and/or liquid vessels of chlorine, bromine, chlorine dioxide, iodine, and/or fluorine.

In an aspect, the various methods of use include the combined and/or sequential application of more than one biocide for synergistic efficacy (which may be referred to as interactive disinfection) in comparison to application of an individual disinfectant as measured by a reduction in application time and/or concentrations of biocides required for application. The methods of use include more than one oxidizing biocide to address variables influencing the efficacy of biocides on microorganisms and other aquatic species, including for example, size and characteristics of the organism, ability to decrease biocide concentration, provide alternative treatment or application, decreasing contact time, and overcoming water quality limitations (e.g., salinity, pH, temperature, oxygen content).

In an aspect, the methods of using combined and/or sequential application of more than one biocide provide less reactive disinfectants (i.e. comparison to chlorine forms in the state of the prior art) for increased efficacy in reducing disinfection byproducts (DBPs), including carcinogenic DBPs formed during disinfection using a non-selective disinfectant species (e.g. chlorine) alone which contact organic substance commonly found in water (e.g. trihalomethanes (THMs), haloacetic acids (HAAs) and adsorbable organic halogens (AOX), such as monochloroacetic acid, trichloromethane, dichloroacetic acid, and trichloroacetic acid). Beneficially, according to the methods of the invention, treatment using biocides may alternate or switch between biocides which do not result in addition and substitution reactions (e.g. chlorine).

In a further aspect, the methods provide more effective control biofilms in a distribution system treated according to the invention.

In an aspect, the various methods of use according to the invention may include a dilution step, wherein the biocides (or one or more of the biocides) are diluted prior to an application of use, for example for disinfecting and/or sanitizing a hard surface. In an aspect, biocide(s) may be diluted to an effective use concentration of less than about 1.0% or about 1,000 mg/L. In some aspects, biocide(s) may be diluted to an effective use concentration of less than about 750 mg/L. In a preferred aspect, the dilution may take place within a biocide generator by supplying a water of dilution. In some aspects, the water of dilution is added inline, in a storage tank prior and/or at dispensing prior to an application of use. In some aspects, the typical dilution factor of a biocide electrolytically generated according to the invention is from about 0.1:100 to about 1:1. In an aspect, the various methods of use may include an alternating contacting step wherein a surface and/or water source is contacted by a first biocide and thereafter by a second biocide (with optional repetition to such contacting). In an aspect, a first step of contacting with chlorine or sodium hypochlorite is alternated with contacting with a second biocide selected from the group consisting of chlorine dioxide, bromine, iodine, fluorine, chloramines and combinations thereof. Such alteration may be employed to reduce costs of chemistries administered to a surface and/or water source in need of chlorination, disinfection and/or sanitation.

Treatment of Water Sources

The methods of the invention solve a need in the art to produce water sources having been disinfected to achieve high inactivation for various pathogens. For example, in the U.S. biocide applications are regulated by the EPA under The Federal Insecticide, Fungicide and Rodenticide Act (FIFRA). Under such regulations biocides cannot be applied outside of the stipulated ranges and must be used in a manner consisting with the FIFRA label, which specifies dosage, time, concentration, and frequency. Moreover, under such regulations the biocide must be applied to the target organism specified on the label.

In an aspect, the biocides generated according to the methods of the invention are suitable for use in disinfection of all types of water, including potable. Potable water types include; atmospheric, surface, spring, and well waters. In an aspect, the chlorine, sodium hypochlorite and/or additional biocides are generated at a point use and provided to a water source in need of disinfection. In some aspects, biocides provided for water disinfection destroy enteric and pathogenic organisms, thereby eliminating and preventing waterborne disease. In further aspects, biocides provided for water disinfection eliminate problems in industrial equipment associated with micro- and macro-fouling. In an aspect, at least 0.1 ppm, at least 0.1 mg/L residual biocide concentration, from about 0.1 to about 5 mg/L is provided to a water source (either continuous or intermittent) in need of disinfection for at least 1 minute, at least 5 minutes, or at least 10 minutes, or at least 30 minutes. As one skilled in the art will ascertain the dosages of biocides will vary with source water conditions and the degree of contamination present.

The methods of the invention may include destroying enteric, pathogenic and/or biofilm-forming organisms. In some aspects, waterborne disease(s) is/are thereby prevented and/or eliminated. The methods are suitable for destroying (i.e. disinfecting) at least the following classes of organisms: filamentous, corrosive, non-spore forming, and/or spore forming bacteria, including for example, sulfur depositing, iron depositing, *Streptomyces, Desulfovibrio, Flavo bacterium, Achromobacter, Aerobacter, Mucoids, Bacillus subtilis, Bacillus megatherium, Bacillus mycoides, Alcaligenes*; pathogenic bacteria, including for example, *Bacillus cerus, Campylobacter jejuni, Listeria monocytogenes, Clostridium perfringens, Clostridium botulinum, Staphylococcus aureus, Salmonella typhosa, Salmonella paratyphii, schottinuller, hirschfeldii C., Legionella pnermophila, Vibrio comma, cholera, Pateruella tulareusis, Brucella melitensis, Pseudomonas pseudomallei, Laptospira icterohaemorragiae, Escherichia coli, Shigella flexneri, dysenteriae, sonnei, paradisinteriae*; pathogenic viruses including for example, Poliovirus (3 types), Echovirus (34 types), Coxsackie Virus A and B (>24 types), Reovirus (6 types), Adenovirus, Hepatitis (2 types); parasitic protozoa, including for example, *Giardia lamblia, Cryptosporidium muris, parvum, Entamoeba histolytica, Ascario lumbriocoides* (round worm), *Naegleria gruberi, fowleri, Acenathamoeba castellani, Taenia saginata* (beef tapeworm); mycotoxins, including for example, *Penicillium viridicatum, citrinum, Aspergillus flavus, parasiticus, Patulin expansum, urticae, Aspergillus ochraceus, Fusarium graminearum*; algae, including for example, eukaryotic organisms ranging from unicellular genera to multicellular forms (e.g. giant kelp), exemplary algae including for example, *Chroococcus, Oscillatoria, Chlorococcus, Ulothrix, Navicula, Fragilaria*; mold, namely spore forming fungi/molds, including for example, *Aspergillus, Penicillium, Trichoderma, Cladosporium, Mucon*; yeasts, including for example, *Monilia, Oospora, Torula, Endomyces, Rhodotorule*; and mollusks, including for example, Zebra Mussels, Eurasian Mussels, Asia Clam, barnacles; etc.

Further benefits of using biocides for disinfection of wastewaters including, for example; odor control, including odors formed in anaerobic conditions, prevention of septicity, control of activated sludge bulking, including improvement of sludge sedimentation rate in activated sludge processes, removal of pollutants, such as tetraethyl lead, cyanides, nitrites, sulfides, aromatic hydrocarbons, phenols, and the like, and cyanide destruction. In an aspect, disinfection of wastewater involves the providing or delivery of an effluent that meets applicable regulatory discharge standards (e.g. EPA National Pollutant Discharge Elimination System (NPDES) requirements) to eliminate or control total and fecal coliform. In an aspect, the chlorine, sodium hypochlorite and/or additional biocides are generated at a point use and provided to a wastewater source in need of chlorinate and disinfection. Beneficially, the methods of providing alternating oxidating biocides to a water source provide synergistic and effective disinfection without producing DBPs. In an aspect of the invention, use of the biocides as set forth herein may beneficially reduce DBPs from 100 to 175 mg/L to less than 0.1 mg/L, such as for example trihalomethanes (THMs).

In other aspects, the methods of the invention may include eliminating undesirable pathogens from drinking water. For example, applications of the methods are suitable for treating drinking water to achieve the following: removing iron and manganese, reducing water turbidity and color, removing odors and flavors, removing hydrocarbons derived from pollution, etc.

In other aspects, the methods of the invention may include eliminating problems associated with micro- and macro-fouling in industrial equipment. As referred to herein, industrial equipment includes, for example, tanks/columns, open basins, pipes, heaters/boilers, pumps/compressors, condensers, heat exchangers, etc. As one skilled in the art ascertains, problems associated with industrial equipment include, for example: fouling, corrosion, protection for corrosive bacteria, wood decay, formation of corrosion cells, formation of gases, and causing illness to susceptible individual by bacteria, algae, fungi/molds, yeasts, and/or mollusk.

In other aspects, the methods of the invention may include treating water utilized in food and beverage processes. Food and beverage applications include, for example: fruit and vegetable processing (whole and cut); poultry chiller tanks and processing; food contact paper manufacture; cleaning pasteurizers, bottle/can warmers and coolers; disinfection of packing operations; flume water control (fresh and processed); mold and odor control; chain and conveyor line lube injection treatment; feed water (primary water) and/or intended for human consumption (i.e. taken from a well and not distributed by a water system); water for general washing purposes (waters for washing or transporting); cleaning in place (CIP) and sanitizing operations; water filtration and distribution system disinfection; equipment disinfection; disinfection of tankers, vehicles and transportation vessels; beverage brewery bottle/can washing; filler head assemblies; water used in processing (e.g. breweries, shrimp and chicken processing); waste water (for disinfection prior to discharge in the environment); cooling water (e.g. tomato preserving industry (evaporator towers), breweries, cheese factories, cooked meat processing industries, and canneries where food is canned after sterilization by heat).

In an aspect, the various methods include employing a biocide generated at a point of use. In an aspect at least one biocide selected from the group consisting of chlorine, sodium hypochlorite, chlorine dioxide, bromine, iodine, fluorine, chloramines and combinations thereof is generated at a point of use. The biocide(s) then contacts a surface and/or water source in need of chlorination, disinfection and/or sanitation.

In an aspect, the generation of the biocides including the steps of providing a divided electrolytic cell, supplying a sodium chloride solution to the cell to generate an elemental chlorine and a sodium hydroxide effluent stream from the electrolytic cell, optionally combining at least a portion of the elemental chlorine stream with the sodium hydroxide stream to form a sodium hypochlorite solution, and combining at least a portion of the elemental chlorine stream with a salt solution. The combining of the elemental chlorine with the salt solutions disclosed herein according to the invention generate an additional biocide.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The degradation of a 12.5% bleach solution at various temperatures was evaluated to assess storage and transportation limitations associated with convention chlorine biocides. Tables 1-3 show calculations obtained from laboratory studies published in the Journal of the American Water Works Association (Gordon et al., "Predicting Liquid Bleach Decomposition," J. Am. Water Works Assoc., 89(4), 142-149, 1997).

TABLE 1

(Degradation of a 12.5% Bleach Solution at 60° F.)

| Concentration | Days | Loss in Concentration |
| --- | --- | --- |
| 12.41% | 7 | 0.72% |
| 12.32% | 15 | 1.53% |
| 12.14% | 30 | 3.04% |
| 11.78% | 60 | 5.99% |

TABLE 2

(Degradation of a 12.5% Bleach Solution at 70° F.)

| Concentration | Days | Loss in Concentration |
| --- | --- | --- |
| 12.32% | 7 | 1.46% |
| 12.13% | 15 | 3.10% |
| 11.77% | 30 | 6.11% |
| 11.08% | 60 | 11.85% |

TABLE 3

(Degradation of a 12.5% Bleach Solution at 80° F.)

| Concentration | Days | Loss in Concentration |
| --- | --- | --- |
| 12.08% | 7 | 3.51% |
| 11.62% | 15 | 7.37% |
| 10.80% | 30 | 14.19% |
| 9.34% | 60 | 26.36% |

As shown, the degradation rate doubles, approximately, for every 10° F. above 60° F. The data in Tables 1-3 demonstrate that storage of bleach at approximately 60° F. (15° C.) will greatly reduce the degradation of the bleach. However, the degradation rates present a significant control reliability concern for apparatus and/or systems employing control logic to maintain a target chlorine dose rate and/or residual concentrations. For example, any underfeed of chlorine for disinfection of a water source and/or surface will result in microbiological growth, whereas any overfeed can result in excess chemical costs and potential damage to the system metallurgy (e.g. corrosion). Such control reliability is further exacerbated by product degradation off-gassing resulting in further disruption (e.g. chemical feed pumps to losing prime and disrupting dosing rate).

The chlorine degradation demonstrated in Tables 1-3 presents another difficulty in that degradation results in chloride ions, known to enhance corrosion caused by free chlorine. For example, chloride ions and free chlorine easily penetrate passive films on metals and allow corrosive attack to occur on system piping (along with penetration of Teflon or similar material coated or encapsulated surfaces).

Accordingly, there is a demonstrated need for biocidal applications that do not rely solely on chlorine disinfectants.

Example 2

Electrolytic Sodium Hypochlorite Generation (State of the Art). Sodium hypochlorite was generated using three common consumables: sodium chloride (salt), water and electricity. NSF-60 certified salt pellets were used in the process. The on-site generation system operated by feeding softened water into a brine tank containing salt pellets. The salt dissolved to form a saturated sodium chloride solution, which was further diluted to the desired salt concentration of approximately 13,000 mg/L. The salt solution was then passed through the anode side of the electrolytic cell at a rate of approximately 90 mL/min and water through the cathode side at a rate of approximately 45 mL/min. A DC current of 40 amps was applied to the electrolytic cell to produce elemental chlorine on the anode side and sodium hydroxide and hydrogen gas on the cathode side of the electrolytic cell according to the following reaction:

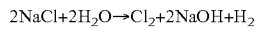

$2NaCl + 2H_2O \rightarrow Cl_2 + 2NaOH + H_2$

Both streams were combined, forming a sodium hypochlorite (bleach) solution, and stored in a day tank.

$Cl_2 + 2NaOH \rightarrow NaOCl + NaCl + H_2O$

The on-site generator continued to operate until the high level position of the tank was reached. A metering pump was used to dose the bleach from the tank to the intended application. When the bleach reached the low level position in the tank, the on-site generator automatically restarted to replenish its supply. The system was fully automated using a control and monitoring system with automated and manual operation features.

Figure 5:
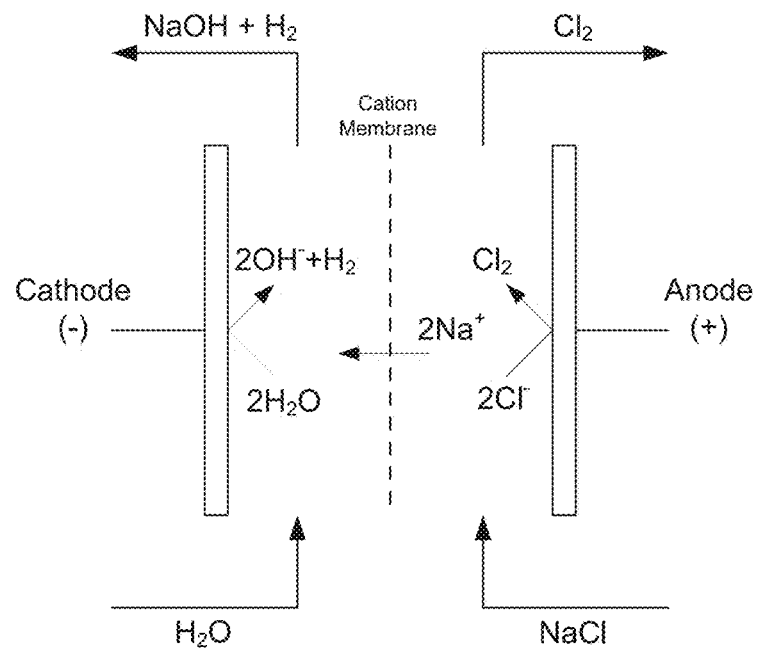
FIG. 5 shows electrolytic chlorine generation according to an embodiment of the present state of the art employing an electrolytic cell.
Figure 6:
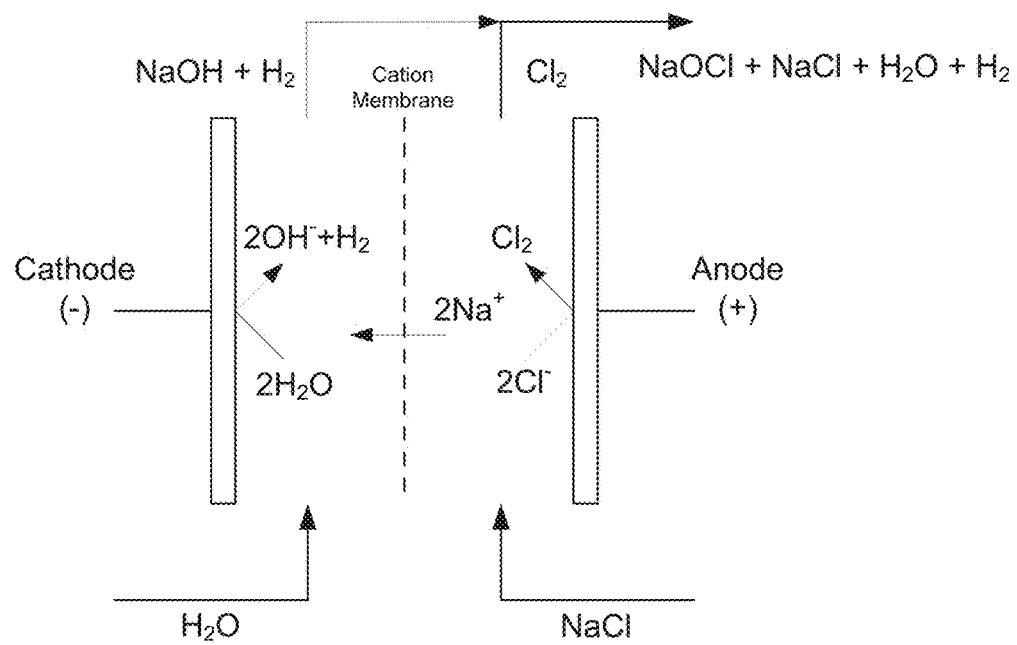
FIG. 6 shows electrolytic sodium hypochlorite generation according to an embodiment of the present state of the art employing an electrolytic cell.

A general view of the electrolytic cell as well as the sodium hypochlorite production are illustrated in FIGS. 5-6.

Example 3

Electrolytic Chlorine and Chlorine Dioxide Generation. An on-site generation system as described in Example 1 was operated by feeding softened water into a brine tank containing salt pellets (NSF-60 certified salt pellets), forming a saturated sodium chloride solution (diluted to approximately 13,000 mg/L). The salt solution was then passed through the anode side of the electrolytic cell at a rate of approximately 90 mL/min and water through the cathode side at a rate of approximately 45 mL/min. A DC current of 40 amps was applied to the electrolytic cell to produce elemental chlorine on the anode side and sodium hydroxide and hydrogen gas on the cathode side of the electrolytic cell. The effluent streams (elemental chlorine and sodium hydroxide) were not combined in this example; however the apparatus can include an output line for storing the generated chlorine as well as a second output line for transporting the chlorine for combination with salt of the additional biocide for generation (e.g. sodium chlorite). A 25 wt % sodium chlorite solution (302.3 g/L) was added to the elemental chlorine stream at a rate of 5.32 mL/min. The sodium chlorite reacted with chlorine to produce chlorine dioxide at a production rate of 3.81 lb/day, according to the following reaction:

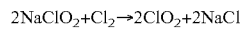

$2NaClO_2 + Cl_2 \rightarrow 2ClO_2 + 2NaCl$

Figure 7:
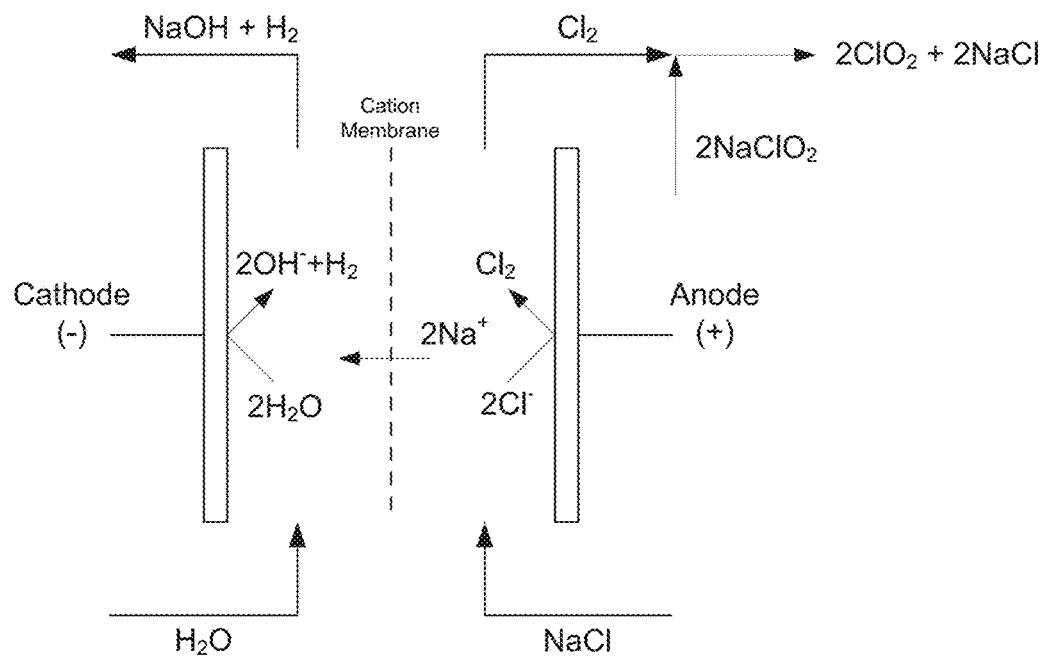
FIG. 7 shows electrolytic chlorine and chlorine dioxide generation according to an embodiment of the present invention.

A further depiction of the chlorine and chlorine dioxide production is illustrated in FIG. 7. Beneficially, the methods of the invention allow the use of chlorine to generate the second biocide chlorine dioxide within a single system.

Example 4

Electrolytic Chlorine and Bromine Generation. The process describe in Example 2 was further employed to generate an additional biocide. Again, the effluent streams (elemental chlorine and sodium hydroxide) were not combined. Acti-Brom (42.8% sodium bromide solution) was added to the elemental chlorine stream at a rate of 4.28 mL/min. The sodium bromide reacted with chlorine to produce bromine at a production rate of 4.51 lb/day, according to the following reaction:

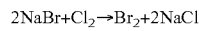

$2NaBr + Cl_2 \rightarrow Br_2 + 2NaCl$

Figure 8:
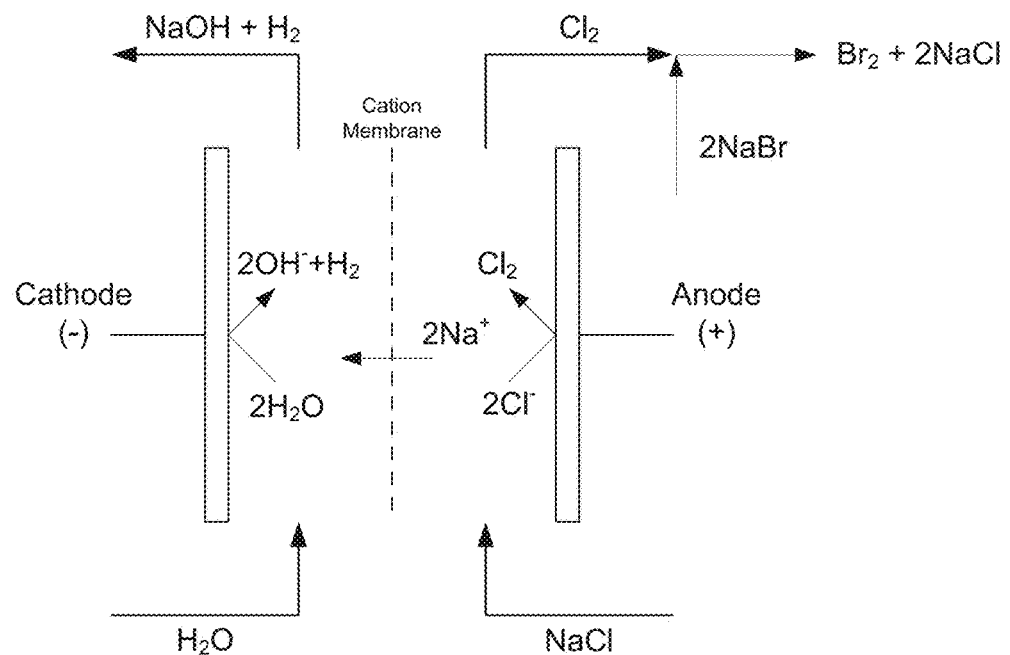
FIG. 8 shows electrolytic chlorine and bromine generation according to an embodiment of the present invention.

A further depiction of the chlorine and bromine production is illustrated in FIG. 8. Beneficially, the methods of the invention allow the use of chlorine to generate the second biocide bromine within a single system.

Example 5

Electrolytic Chlorine and Iodine Generation. The process describe in Example 2 was further employed to generation an additional biocide showing further diversity of the methods of the invention. Again, the effluent streams (elemental chlorine and sodium hydroxide) were not combined. A 20% potassium iodide solution (200 g/L) was added to the elemental chlorine stream at a rate of 14.77 mL/min. The potassium iodide reacted with chlorine to produce iodine at a production rate of 4.68 lb/day, according to the following reaction:

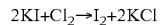

$2KI + Cl_2 \rightarrow I_2 + 2KCl$

Figure 9:
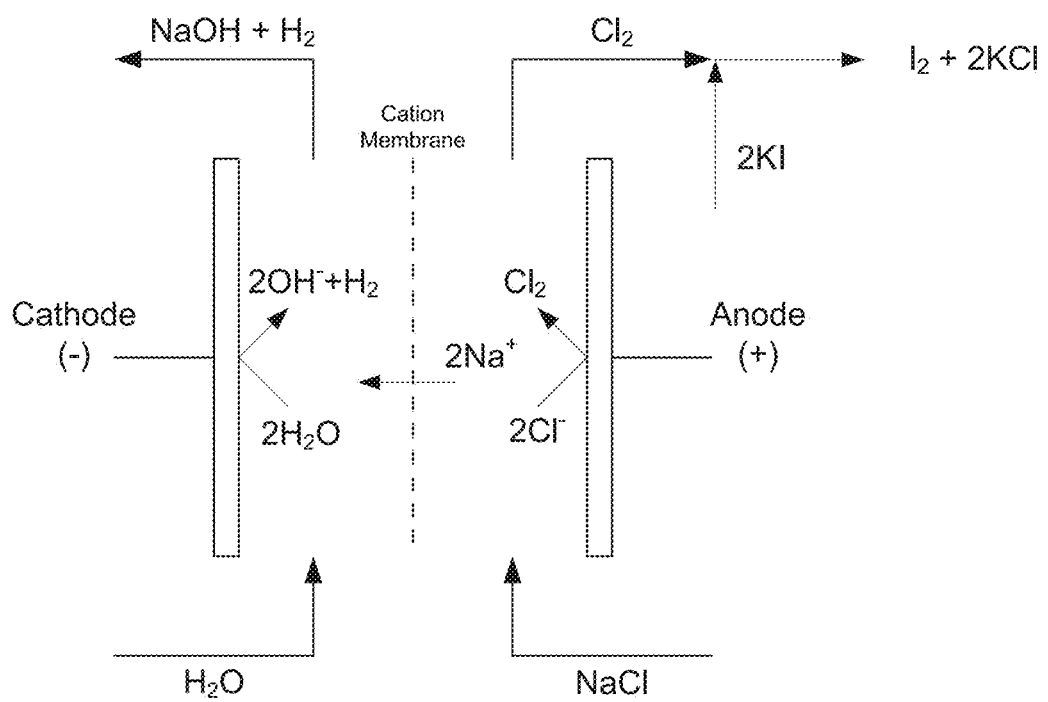
FIG. 9 shows electrolytic chlorine and iodine generation according to an embodiment of the present invention.

A further depiction of the chlorine and bromine production is illustrated in FIG. 9. Beneficially, the methods of the invention allow the use of chlorine to generate the second biocide bromine within a single system.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A method of generating a dual biocide comprising:
   providing a divided electrolytic cell;
   supplying a sodium chloride solution to the cell to generate an elemental chlorine and a sodium hydroxide effluent stream from the electrolytic cell, wherein the electrolytic cell comprises an anode chamber and a cathode chamber separated by a cation exchange membrane, and wherein the cathode chamber contains a cathode and the anode chamber contains an anode;

applying a potential to the electrolytic cell:

combining at least a portion of the elemental chlorine stream with the sodium hydroxide stream to form a first biocide sodium hypochlorite solution; and combining at least a portion of the elemental chlorine stream with a salt solution to generate a second biocide at a point of use, wherein a sub-stoichiometric amount of said salt solution generates said second biocide in combination with chlorine and a stoichiometric amount of said salt solution generates said second biocide alone.

2. The method of claim 1, wherein the salt solution contains a member selected from the group consisting of chlorite, bromide, iodide, fluoride, ammonia and combinations thereof.

3. The method of claim 2, wherein the combination of the elemental chlorine with the salt solution generates chlorine dioxide, bromine, iodine, fluorine, chloramines or combinations thereof.

4. The method of claim 1, wherein the cation exchange membrane is a cross-linked perfluorinated polymer backbone with attached sulfonic acid groups.

5. The method of claim 1, wherein the operational current density of the electrolytic cell is less than about 1.0 amp per square inch and/or the electrolytic cell generates a concentration of free available chlorine of less than about 12 grams per liter.

6. The method of claim 1, further comprising measuring at least one of the conditions selected from the group consisting of temperature, volume, flow, pressure, and combinations thereof, and employing at least one member selected from the group consisting of flow meter, rotameter, pressure transducer, thermometer, and combinations thereof.

7. The method of claim 6, wherein at least one of the following is measured: flow meter output, temperature of the electrolytic cell, temperature of electrolyte, temperature of chlorine, brine pump velocity, brine flow rate, current density in the electrolytic cell, water pressure, and incoming water flow rate.

8. A method of providing a dual biocide at a point of use comprising:

providing an electrolytic cell having an anode chamber and a cathode chamber separated by a cation exchange membrane, wherein the cathode chamber contains a cathode and the anode chamber contains an anode;

supplying a sodium chloride solution to the cell to generate an elemental chlorine and a sodium hydroxide effluent stream from the electrolytic cell;

applying a potential to the electrolytic cell;

combining at least a portion of the elemental chlorine stream with the sodium hydroxide stream to form a first biocide sodium hypochlorite solution;

combining at least a portion of the elemental chlorine stream with a salt solution, wherein the salt solution contains a member selected from the group consisting of chlorite, bromide, iodide, fluoride, ammonia and combinations thereof;

generating a second biocide selected from the group consisting of chlorine dioxide, bromine, iodine, fluorine, chloramine and combinations thereof; and providing the biocides to an application of use.

9. The method of claim 8, wherein the cation exchange membrane is a cross-linked perfluorinated polymer backbone with attached sulfonic acid groups, and wherein the electrolytic cell generates a concentration of free available chlorine of less than about 12 grams per liter (g/L).

10. The method of claim 8, wherein a stoichiometric amount of said salt solution is provided to said elemental chlorine stream and generates said second biocide without additional chlorine generated.

11. The method of claim 8, further comprising the step of determining the oxidant demand of the application of use for the biocides.

12. The method of claim 8, further comprising measuring at least one of the conditions selected from the group consisting of temperature, volume, flow, pressure, and combinations thereof, and employing at least one member selected from the group consisting of flow meter, rotameter, pressure transducer, thermometer, and combinations thereof.

13. The method of claim 12, wherein at least one of the following is measured: flow meter output, temperature of the electrolytic cell, temperature of electrolyte, temperature of chlorine, brine pump velocity, brine flow rate, current density in the electrolytic cell, water pressure, and incoming water flow rate.

14. A method of chlorinating, disinfecting and/or sanitizing employing a biocide generated at a point of use comprising:

generating at least one biocide selected from the group consisting of chlorine, sodium hypochlorite, chlorine dioxide, bromine, iodine, fluorine, chloramines and combinations thereof at a point of use according to the method of claim 1; and contacting a surface and/or water source in need of chlorination, disinfection and/or sanitation with the biocide to provide at least 0.1 mg/L residual biocide concentration for at least 1 minute.

15. The method of 14, further comprising the step of alternating between contacting a surface and/or water source with chlorine or sodium hypochlorite and a second biocide selected from the group consisting of chlorine dioxide, bromine, iodine, fluorine, chloramines and combinations thereof.

16. The method of claim 14, wherein a potable water source is contacted with the biocides for disinfection.

17. The method of claim 14, wherein a wastewater source is contacted with the biocides for chlorination for odor control, prevention of septicity, control of activated sludge bulking, removal of pollutants, eliminating total and fecal coliform, and/or cyanide destruction.

18. The method of claim 14, wherein the surface is a hard surface selected from a clean-in-place system, food and beverage processing equipment or system, water filtration and distribution system, tank, vehicle or transportation vessel, beverage brewery bottle/can washing system, and filling assemblies.

19. The method of claim 14, further comprising the step of determining the oxidant demand of the application of use for the biocides.

\* \* \* \* \*